Figure 1:
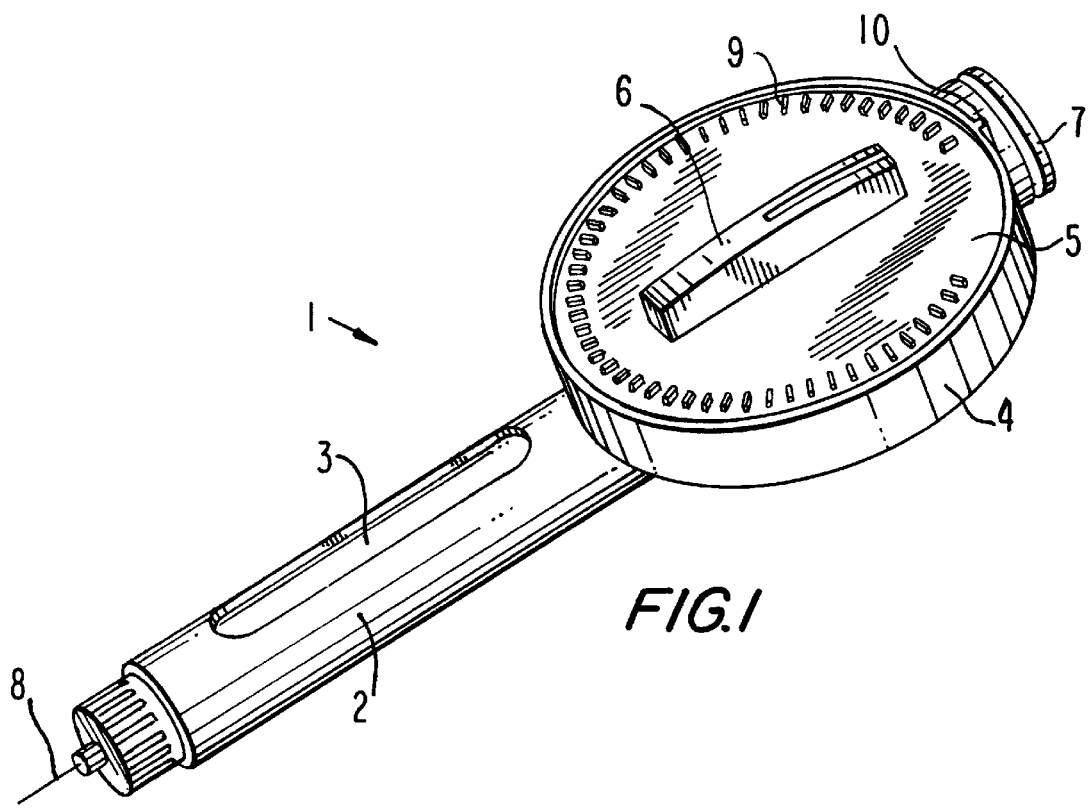

United States Patent [19]
Hansen

[11] Patent Number: 6,074,372
[45] Date of Patent: Jun. 13, 2000

[54] DOSE SETTING MECHANISM AND AN INJECTION SYRINGE HAVING SUCH A DOSE SETTING MECHANISM

[75] Inventor: Steffen Hansen, Hillerød, Denmark

[73] Assignee: Novo Nordisk A/S, Bagsværd, Denmark

[21] Appl. No.: 09/089,821

[22] Filed: Jun. 3, 1998

Related U.S. Application Data

[60] Provisional application No. 60/052,978, Jun. 13, 1997.

[30] Foreign Application Priority Data

Jun. 9, 1997 [DK] Denmark .................................. 0674/97

[51] Int. Cl.⁷ ........................................................ A61M 5/00
[52] U.S. Cl. ............................................. 604/211; 604/224
[58] Field of Search ........................... 604/207–211, 224

[56] References Cited

U.S. PATENT DOCUMENTS 5,947,934  9/1999  Hansen et al. ............................ 604/207

FOREIGN PATENT DOCUMENTS

WO 94/13343  6/1994  WIPO .

*Primary Examiner*—Corrine McDermott
*Attorney, Agent, or Firm*—Steve T. Zelson, Esq.

[57] ABSTRACT

A dose setting mechanism for a drug administration device and an injection syringe having such a dose setting mechanism are provided. The injection syringe has a housing accommodating an ampoule (3) containing medicine sufficient for a number of dosed injections, an injection press button (7), a piston rod (13) for co-operation with a piston in the ampoule (3) when injecting, and a dose setting mechanism comprising a rotatable dose setting element (5) interconnected with the press button. The dose setting mechanism further comprises a dose administration wheel (11) connected with the piston rod (13) and a coupling ring (12) connected with the dose setting element (5) and the press button (7). One of the dose administration wheel (11) and the coupling ring (12) at least partly surrounds the other, and the dose administration wheel (11) and the coupling ring (12) are arranged such that rotation of the dose setting element (5) allows the coupling ring (12) to be rotated in either direction in relation to the dose administration wheel (11), while activation of the press button (7), and thereby rotation of the coupling ring (12), causes the dose administration wheel (11) to be rotated.

9 Claims, 2 Drawing Sheets

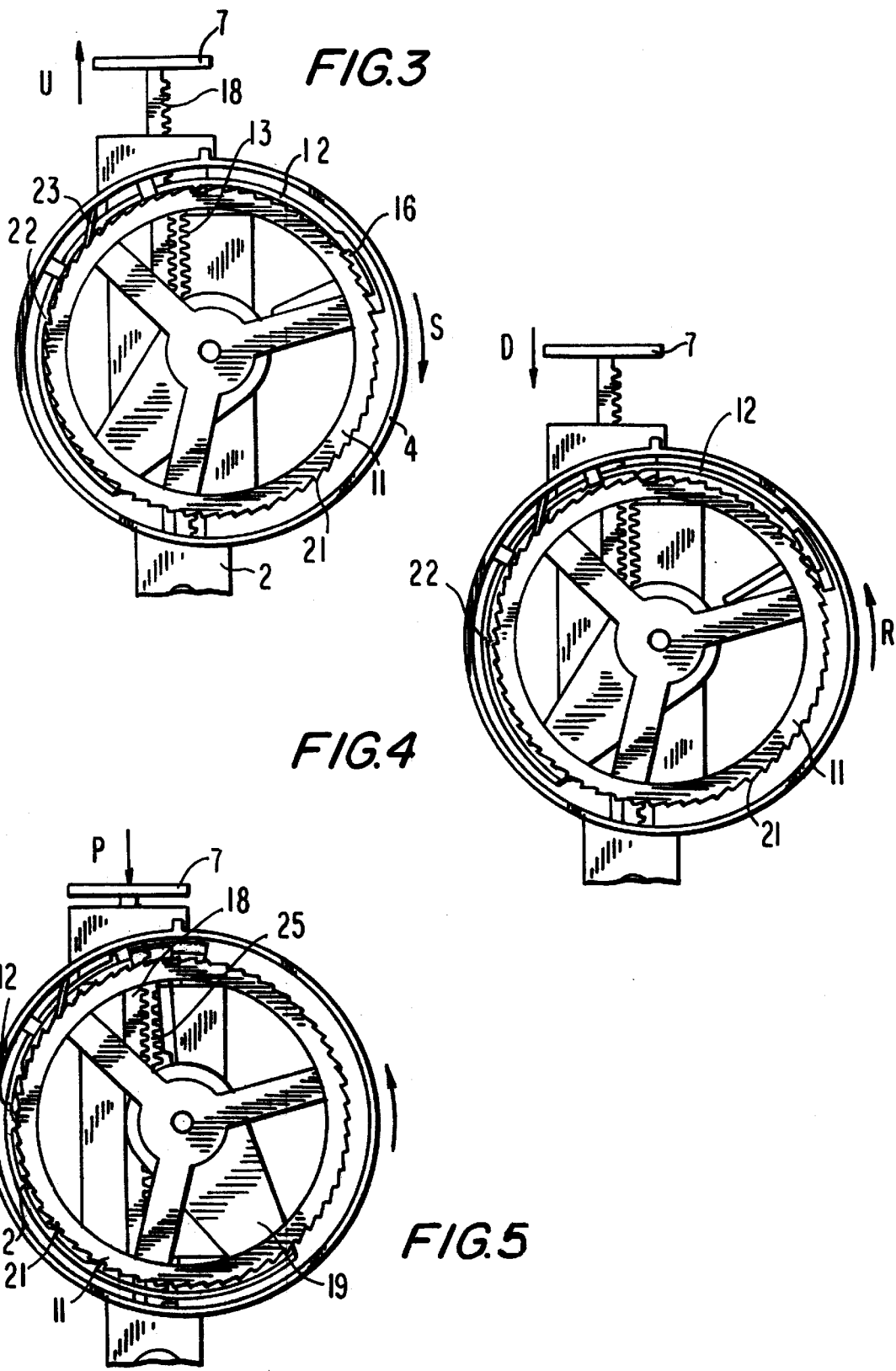

US 6,074,372

DOSE SETTING MECHANISM AND AN INJECTION SYRINGE HAVING SUCH A DOSE SETTING MECHANISM

CROSS-REFERENCE TO RELATED APPLICATIONS

This application claims priority under 35 U.S.C. 119 of Danish application No. 0674/97 filed Jun. 9, 1997, and U.S. provisional application No. 60/052,978 filed Jun. 13, 1997, the contents of which are fully incorporated herein by reference.

A dose setting mechanism and an injection syringe having such a dose setting mechanism.

The invention relates to a dose setting mechanism for a drug administration device having a housing and a press button connectable with a piston rod for administration of a set dose from a container, said dose setting mechanism comprising a rotatable dose setting element interconnected with the press button.

Drug administration devices having dose setting mechanisms are known in a number of different types, e.g. syringes, inhalators, atomisers, etc. The aim of these drug administration devices is to make the user capable of setting an individual dose of drug to be administered.

Best known in the art are injection syringes for use by patients, mainly diabetics, who have to inject themselves with individually set doses of medicine, e.g. insulin. Such syringes are often given a shape like a pen in order to be carried by the patient all through the day and are always ready for use.

When the dose is to be set in these pen-shaped injection syringes, a cap covering the needle portion of the syringe is rotated, causing a press button at the opposite end of the injection syringe to move outwards. The press button often has a scale on the shaft connecting the press button with the interior of the injection syringe, and the dose set can be read on this scale. After setting the dose, the user removes the cap from the needle portion, inserts the needle in the area to be injected and injects the medicine by pressing the press button. When the press button reaches its bottom, the set dose has been injected.

One disadvantage of these pen-shaped injection syringes is that the scale on the shaft of the press button has rather small divisions and digits owing to the limitations set by the perimeter of the shaft. If the user is visually impaired, as can often be the case with diabetics, this may cause wrong dose settings having serious consequences for the user.

An attempt to overcome this disadvantage is disclosed in DE Al 4 208 677 showing an injection syringe provided with a dose setting scale having large digits. The dose setting device consists of a box-like container in which an injection syringe may be placed. When setting the dose, a stop is moved on the piston rod of the injection syringe until the right dose, as read on the scale, has been set. Then the user removes the injection syringe from the dose setting device and injects himself like with an ordinary injection syringe, while the stop on the piston rod determines the dose being injected.

All the known injection syringes having dose setting devices have the disadvantage that the dose setting device, or at least a part of it, has to be removed from the injection syringe after the dose has been set but before injection can take place. Some of the injection syringes, as is the case with the one disclosed in DE Al 4 208 677, even have the disadvantage that the set dose cannot be checked after the dose setting device has been removed, as the injection syringe itself has no scaling means.

It is an object of the present invention to provide a dose setting mechanism that can be built into a drug administration device, e.g. an injection syringe, is non-removable from it and provides the possibility of setting a dose and regretting the set dose. Further, there should always be full correspondence between the movement of the dose setting element and the movement of the press button in order to assure the user of the dose set and the dose administered.

This is obtained by a dose setting mechanism of the type mentioned in the opening paragraph of this specification, which is characterized in that the dose setting mechanism further comprises a dose administration wheel connected with said piston rod and a coupling ring connected with the dose setting element and the press button, one of said dose administration wheel and said coupling ring at least partly surrounding the other, said dose administration wheel and said coupling ring being arranged such that rotation of the dose setting element allows the coupling ring to be rotated in either direction in relation to the dose administration wheel, while activation of the press button, and thereby rotation of the coupling ring, causes the dose administration wheel to be rotated.

Arranging the dose setting mechanism in this way provides a dose setting mechanism which can be fully built into a drug administration device, e.g. an injection syringe, and has the possibility of setting a dose and regretting the set dose. As the dose setting element is connected with the coupling ring which is in turn connected with the press button, full correspondence between the movement of the dose setting element and the movement of the press button is achieved.

In order to achieve the co-operation between the dose administration wheel and the coupling ring, these parts may advantageously be arranged as stated in claim 2. Claim 3 discloses further arrangements according to a preferred embodiment. By incorporating all these features a particularly simple construction needing only four parts to build the dose setting mechanism is achieved, i.e. the dose setting element, the dose administration wheel, the coupling ring and the press button.

The invention also relates to an injection syringe comprising a housing accommodating an ampoule containing medicine sufficient for a number of dosed injections, an injection press button, a piston rod for co-operation with a piston in the ampoule when injecting, and a dose setting mechanism comprising a rotatable dose setting element interconnected with the press button. The injection syringe is further characterized in that the dose setting mechanism includes the features mentioned in claim 1.

By arranging the injection syringe in this way, an injection syringe is obtained having a built-in dose setting mechanism wish the possibility of setting a dose and reducing the set dose. As the dose setting element is connected with the coupling ring which is in turn connected with the press button, full correspondence between the movement of the dose setting element and the movement of the press button is achieved.

The connection between the different parts of the dose setting mechanism is preferably as mentioned in claims 5 and 6, giving the advantages mentioned earlier.

In a preferred embodiment the housing has means for preventing the dose administration wheel from being rotated in one direction corresponding to withdrawal of the piston from the ampoule. This ensures, when the dose setting mechanism is used in an injection syringe, that the piston rod can never be withdrawn from the piston in the ampoule but is always in firm contact with the piston. If the piston rod could be withdrawn from the piston, the dose injected would not correspond to the dose set, owing to the gap between the piston rod and the piston.

The dose administration wheel is preferably connected with the piston rod via a gear wheel provided at the center of the dose administration wheel.

Preferably the injection syringe is provided with a scale and a pointer indicating the dose set when the dose setting element is rotated.

Figure 2:
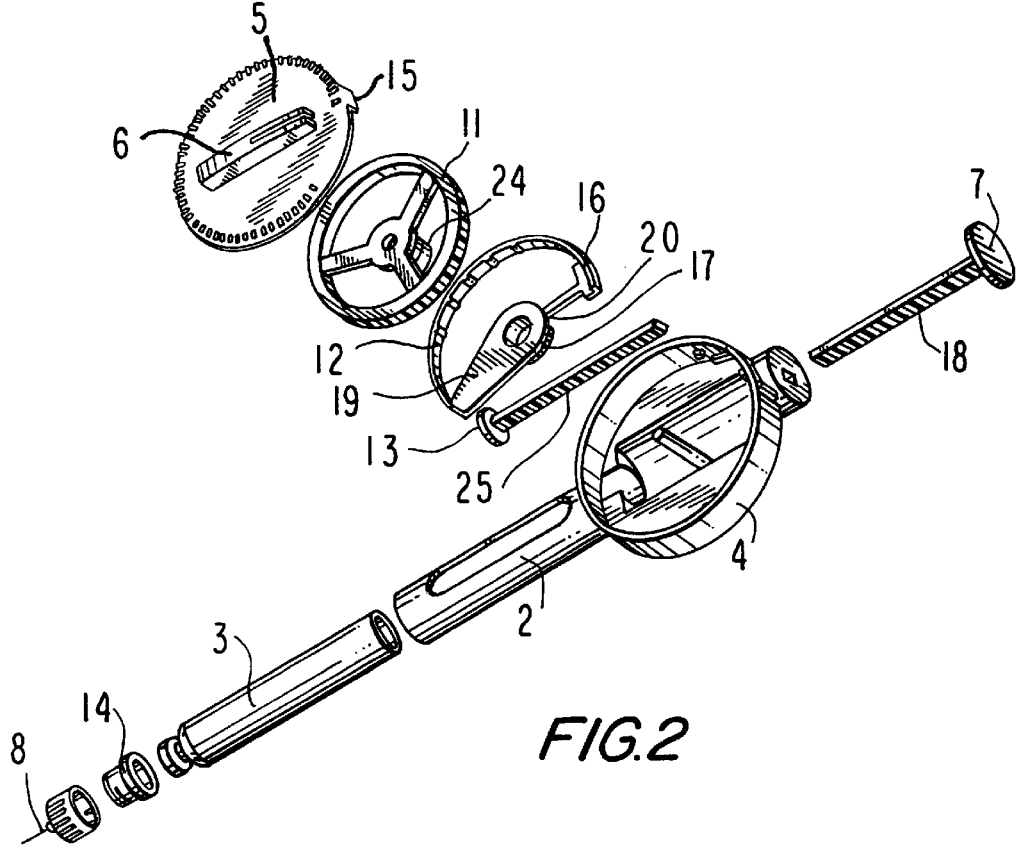

More advantages and the mode of operation of the dose setting mechanism will be described more fully in the following with reference to the drawings in which FIG. 1 shows a top perspective view of an embodiment of an injection syringe having a dose setting mechanism according to the invention, FIG. 2 shows an exploded view of an embodiment of an injection syringe having a dose setting mechanism according to the invention, FIG. 3 shows the dose setting mechanism when setting a dose, FIG. 4 shows the dose setting mechanism when reducing a set dose, and FIG. 5 shows the dose setting mechanism when administering a set dose.

FIG. 1 shows an injection syringe 1 having a dose setting mechanism according to the present invention. The syringe has a first housing part 2 containing an ampoule 3 with medicine, e.g. insulin, the ampoule 3 being seen through a window in the first housing part 2, and a second housing part 4 embracing the dose setting mechanism.

The first housing part 2 is generally pen-shaped, as is known from commercially available injection syringes. The syringe further comprises a dose setting mechanism, of which a rotatable, disc-shaped dose setting element 5 having a finger grip 6 and a press button 7 for injection are seen. Further, a needle 8 extending from the lower end of the injection syringe 1 is shown.

The size of the shown embodiment of an injection syringe 1 and in particular of the dose setting element 5 is such that it fits the user's hand, both when setting a dose of medicine by holding the injection syringe 1 in one hand and setting the dose by rotating the dose setting element 5 with the other hand, and when injecting the set dose by holding the injection syringe 1 in one hand and pressing the press button 7 with the thumb of the same hand.

A scale 9 is provided on the dose setting element 5, and a pointer 10 is provided at the second housing part 4.

FIG. 2 shows the injection syringe 1 in an exploded view showing again the first and second housing parts 2 and 4, the ampoule 3, the dose setting element 5, the press button 7 and the needle 8. The injection syringe 1 further comprises a dose administration wheel 11, a coupling ring 12, a piston rod 13 and a needle coupling part 14.

The dose setting mechanism comprises the dose setting element 5, the dose administration wheel 11, the coupling ring 12 and the press button 7. These parts will be described in more detail in the following as these parts constitute a preferred embodiment of the invention.

The dose setting element 5 is disc-shaped having a finger grip 6 on its upper side and a downwardly projecting tenon 15 at the periphery, said tenon 15 interacting with a notch 16 provided at the rim of the coupling ring 12. The coupling ring 12 is in turn in engagement with the press button 7 via a gear wheel 17 provided at the hub of the coupling ring 12 and a toothed part 18 of the press button 7.

As the dose setting element 5 is connected with the coupling ring 12 which is in turn connected with the press button 7, full correspondence between the movement of the dose setting element 5 and the movement of the press button 7 is achieved. This means that whenever the dose setting element 5 is rotated for setting or reducing a dose, the press button 7 moves out of or into the housing of the injection syringe 1. Similarly, when the press button 7 is pressed in order to inject a set dose, the dose setting element 5 rotates back to its initial position. This means that the user can visually observe that the set dose is injected during the injection act.

The coupling ring 12 consists of a ring segment connected with a hub in each end thereof. At one end the ring segment is connected rigidly to the hub via a rigid part 19, and at the other end the ring segment is connected flexibly with the hub via a flexible part 20. The flexible part 20 is included for facilitating the mounting of the coupling ring, but it may be omitted without changing the working of the dose setting mechanism.

The interaction between the coupling ring 12 and the dose administration wheel 11 will now be explained fully with reference to FIGS. 3–5.

FIG. 3 is a top view of the dose setting mechanism when a dose is set, showing the first and second housing parts 2 and 4, the dose administration wheel 11, the coupling ring 12, the top part of the piston rod 13, the press button 7 and its toothed part 18. The dose setting element 5 is omitted in order to show the interior of the dose setting mechanism, but in use its downwards projecting tenon 15 is in permanent engagement with the notch 16 provided at the rim of the coupling ring 12.

The coupling ring 12 is formed in such a way that it partly surrounds the dose administration wheel 11, and it is seen that the dose administration wheel 11 is provided with barbs 21 at is outer periphery, and that a part of the coupling ring 12 is provided with similar barbs 22.

When a dose is to be set, the dose setting element 5 is rotated clockwise according to the arrow S. This causes the coupling ring 12 to be rotated clockwise, the barbs 22 of the coupling ring 12 sliding over the barbs 21 of the dose administration wheel 11. The second housing part 4 is provided with an inwardly projecting pawl 23, which, in co-operation with the barbs 21 provided on the dose administration wheel 11, prevents the dose administration wheel 11 from being rotated clockwise, which would cause the piston rod 13 to be withdrawn from the ampoule 6.

Rotating the coupling ring 12 causes the press button 7 to move upwards according to the arrow U due to the engagement of the gear wheel 17 (FIG. 2) on the coupling ring 12 and the toothed part 18 of the press button 7.

If the set dose is reduced, the dose setting element 5 is rotated anti-clockwise according to the arrow R in FIG. 4. Due to the flexible part 20 of the coupling ring 12 (FIG. 2), the coupling ring 12 expands outwards, as shown, allowing the barbs 22 to slide over the barbs 21 of the dose administration wheel 11. Hence the dose administration wheel 11 is not affected by this anticlockwise rotation of the coupling ring 12.

The anti-clockwise rotation of the dose setting element 5 causes the press button 7 to move downwards according to the arrow D. Some type of resistance against movement of the press button 7 may be provided in order to ensure that the coupling ring 12 expands outwards when reducing a set dose.

When a set dose is to be injected, the press button 7 is pressed downwards according to the arrow P in FIG. 5.

This causes the coupling ring 12 to be rotated in the anti-clockwise direction as indicated by the arrow I due to the engagement of the toothed part 18 of the press button 7 with the gear wheel 17 (FIG. 2) of the coupling ring 12. Due to the fact that the rotating force from the press button 7 is transferred to the ring segment of the coupling ring 12 via the rigid part 19, the ring segment is not expanded, as was the case when reducing a set dose by rotating the dose setting element 5 anticlockwise, but is tightened around the dose administration wheel 11, causing the barbs 22 of the coupling ring 12 to engage the barbs 21 of the dose administration wheel 11.

Some type of resistance against movement of the coupling ring 12 may be provided at the flexible connected end of its ring segment in order to ensure that it tightens around the dose administration wheel 11 when injecting a set dose.

The engagement between the barbs 22 of the coupling ring 12 and the barbs 21 of the dose administration wheel 11 causes the dose administration wheel 11 to rotate anticlockwise, which in turn causes the piston rod 13 to move forwards in the ampoule 3 due to the interaction of a gear wheel 24 provided at the hub of the dose administration wheel 11 (FIG. 2) and a toothed part 25 of the piston rod 13.

When the injection has been completed, the press button 7 and the dose setting element 5 have returned to their initial positions, ready for another dose setting.

If the injection syringe 1 is to be used by diabetics needing regular injections of insulin, the barbs 21 are preferably of a size corresponding to 1 IU (International Unit). Thereby, each click heard when setting a dose, corresponds to 1 IU, giving the user an audible indication of the dose set together with the visual indication on the scale 9. It further means that the dose can be set very precise y as an integer of International Units.

In the shown embodiment the coupling ring 12 surrounds the dose administration wheel 11. In an alternative embodiment the dose administration wheel surrounds the coupling ring, the dose administration wheel being provided with barbs on its inner periphery, and the coupling ring being provided with barbs on its outer periphery. Hence, if a set dose is to be reduced, the coupling ring must be arranged in such a manner as not to expand but to contract, allowing the barbs of the dose administration wheel and the coupling ring to slide in relation to each other.

The design of the injection syringe need not be pen-shaped as shown, but can be of a compact form having a flexible piston rod surrounding the gear wheel of the dose administration wheel. This provides an injection syringe which is a very handy unit having a size that fits an adult's hand.

In a special embodiment of this type of injection syringe, an extra gear wheel may be arranged between the gear wheel of the dose administration wheel and the flexible piston rod in order to ensure that a relatively large change in the angular position of the dose setting element only causes a small change in the amount of medicine to be injected. Hence, the dose setting can be performed extremely precisely.

Preferably the injection syringe 1 as a whole is made of a plastics material in order to make the disposal after use environmentally correct, but it may also be made of other materials such as metals or any combination of materials.

The injection syringe may be of the disposable type, or it may be of a reusable type in which the ampoule can be replaced when emptied. However, the reusable type requires a special arrangement for retracting the piston rod from its foremost position.

Although the dose setting mechanism has been described in relation to an injection syringe, the dose setting mechanism may be applied to other drug administration devices in which individual doses of drug to be administered can be set.

What is claimed is:

1. A drug administration device comprising a housing and a dose setting mechanism, wherein said dose setting mechanism includes:
    a press button (7) connectable with a piston rod (13) for administration of a set dose from a container,
    a rotatable dose setting element (5) interconnected with said press button (7),
    a dose administration wheel (11) connected with said piston rod (13), and
    a coupling ring (12) connected with the dose setting element (5) and the press button (7) such that rotation of the dose setting element and coupling ring in a first rotational direction moves the press button in one direction, and movement of the press button in an opposite direction rotates said dose settings element and coupling ring in a second rotational direction, wherein one of said dose administration wheel (11) and said coupling ring (12) at least partly surrounds the other, said dose administration wheel (11) and said coupling ring (12) being arranged such that rotation of the dose setting element (5) allows the coupling ring (12) to be rotated in either direction in relation to the dose administration wheel (11), while activation of the press button (7), and thereby rotation of the coupling ring (12), causes the dose administration wheel (11) to be rotated.

2. The drug administration device according to claim 1, wherein the dose administration wheel (11) has an outer periphery provided with barbs (21) wherein the coupling ring (12) includes a hub and a ring segment having opposite ends and an inner side which partly surrounds the dose administration wheel (11), wherein said ring segment is rigidly connected with said hub at one of its ends and flexibly connected to said hub at the other of its ends, said ring segment being provided with barbs (22) over at least part of its inner side, and wherein the dose setting element (5) is connected to the coupling, ring (12) at the end of the ring segment which is flexibly connected with the hub.

3. The drug administration device according to claim 2, wherein the coupling ring (12) has a center containing a gear wheel (17), and wherein the press button (7) includes a toothed part (18) connected with the gear wheel (17).

4. An injection syringe (1) comprising a housing accommodating an ampoule (3) containing a piston and medicine sufficient for a number of dosed injections, an injection press button (7), a piston rod (13) for co-operation with the piston in the ampoule (3) when injecting, and a dose setting mechanism comprising a rotatable dose setting element (5) interconnected with said press button (7), characterized in that the dose setting mechanism further comprises a dose administration wheel (11) connected with said piston rod (13) and a coupling ring (12) connected with the dose setting element (5) and the press button (7), one of said dose administration wheel (11) and said coupling ring (12) at least partly surrounding the other, said dose administration wheel (11) and said coupling ring (12) being arranged such that rotation of the dose setting element (5) allows the coupling ring (12) to be rotated in either direction in relation to th(e dose administration wheel (11), while activation of the press button (7), and thereby rotation of the coupling ring (12), causes the dose administration wheel (11) to be rotated.

5. The injection syringe according to claim 4, characterized in that the dose administration wheel (11) has an outer periphery provided with barbs (21), wherein the coupling ring (12) includes a hub and a ring segment having opposite ends and an inner side which partly surrounds the dose administration wheel (11), wherein said ring segment is rigidly connected with said hub at one of its ends and flexibly connected to said hub at the other of its ends, said ring segment being provided with barbs (22) over at least part of its inner side, and wherein the dose setting element (5) is connected to the coupling ring (12) at the end of the ring segment which is flexibly connected with the hub.

6. The injection syringe according to claim 5, characterized in that the coupling ring (12) has a center containing a gear wheel (17), and wherein the press button (7) includes a toothed part (18) connected with the gear wheel (17).

7. The injection syringe according to claim 4, wherein the dose administration wheel rotates in a first direction for infecting medicine, and characterized in that the dose administration wheel (11) and the housing have cooperating means for preventing the dose administration wheel (11) from being rotated in the opposite direction in response to rotation of the dose setting element (5).

8. The injection syringe according to claim 4, characterized in that the dose administration wheel (11) has a center containing a gear wheel (24) connected with the piston rod (13).

9. The injection syringe according to claim 4, characterized in that the dose setting element (5) is provided with a scale (9), and that the housing is provided with a pointer (10) pointing on said scale (9), said pointer (10) indicating the dose set when the dose setting element (5) is rotated.

* * * * *